United States Patent
Janko et al.

(10) Patent No.: US 8,246,762 B2
(45) Date of Patent: Aug. 21, 2012

(54) IMPLANTABLE MEDICAL DEVICES COMPRISING BIO-DEGRADABLE ALLOYS

(75) Inventors: Gordon F. Janko, Poway, CA (US); Herbert R. Radisch, Jr., San Diego, CA (US); Thomas A. Trozera, Del Mar, CA (US)

(73) Assignee: Bio DG, Inc., Poway, CA (US)

( * ) Notice: Subject to any disclaimer, the term of this patent is extended or adjusted under 35 U.S.C. 154(b) by 172 days.

(21) Appl. No.: 12/684,081

(22) Filed: Jan. 7, 2010

(65) Prior Publication Data
US 2010/0174367 A1 Jul. 8, 2010

Related U.S. Application Data

(60) Provisional application No. 61/143,378, filed on Jan. 8, 2009, provisional application No. 61/168,554, filed on Apr. 10, 2009, provisional application No. 61/260,363, filed on Nov. 11, 2009.

(51) Int. Cl.
*C22C 38/04* (2006.01)
*C22C 38/10* (2006.01)
*C22C 38/18* (2006.01)
*C22C 38/40* (2006.01)
*C22C 38/12* (2006.01)
*C22C 38/14* (2006.01)

(52) U.S. Cl. ........ 148/320; 148/325; 148/327; 148/329; 148/333; 148/334; 148/335; 148/337; 623/924; 623/1.2

(58) Field of Classification Search ............ 148/320, 148/333–337, 325, 327, 329; 420/104–128; 623/1.2, 924
See application file for complete search history.

(56) References Cited

U.S. PATENT DOCUMENTS

| | | | |
|---|---|---|---|
| 5,425,769 A | 6/1995 | Snyders, Jr. | |
| 5,932,459 A | 8/1999 | Sittinger et al. | |
| 6,368,356 B1 | 4/2002 | Zhong et al. | |
| 6,649,631 B1 | 11/2003 | Orme et al. | |
| 7,268,205 B2 | 9/2007 | Williams et al. | |
| 7,601,230 B2 | 10/2009 | Craig | |
| 8,002,909 B2 * | 8/2011 | Craig | 148/333 |
| 2004/0138695 A1 * | 7/2004 | Li et al. | 606/200 |
| 2006/0020317 A1 | 1/2006 | Flach et al. | |
| 2007/0156231 A1 | 7/2007 | Weber | |
| 2008/0015683 A1 * | 1/2008 | Kramer-Brown et al. | 623/1.15 |
| 2008/0069718 A1 | 3/2008 | Craig | |
| 2009/0198320 A1 * | 8/2009 | Mueller et al. | 623/1.38 |
| 2010/0076556 A1 * | 3/2010 | Tomantschger et al. | 623/11.11 |

FOREIGN PATENT DOCUMENTS

JP 2006026418 A 2/2006

OTHER PUBLICATIONS

Hermawan, et al. Development of degradable Fe-35Mn alloy for biomedical application. Advanced Mat. Res. vols. 15-17, 107-112 (2007).
Hermawan et al., Iron-manganese: new class of metallic degradable biomaterials prepared by powder metallurgy. Powder Metallurgy, vol. 51, No. 1, 38-45 (2008).
Issel, Anne L. Lim, Biocompatibility of Stent Materials, MURJ, 2004, pp. 33-37; vol. 11.
PCT/US2010/020396 ISR and Written Opinion, mailed Sep. 29, 2010.

* cited by examiner

*Primary Examiner* — Deborah Yee
(74) *Attorney, Agent, or Firm* — Cooley LLP

(57) ABSTRACT

The invention provides medical devices comprising high-strength alloys which degrade over time in the body of a human or animal, at controlled degradation rates, without generating emboli. In one embodiment the alloy is formed into a bone fixation device such as an anchor, screw, plate, support or rod. In another embodiment the alloy is formed into a tissue fastening device such as staple. In yet another embodiment, the alloy is formed into a dental implant or a stent.

20 Claims, No Drawings

IMPLANTABLE MEDICAL DEVICES COMPRISING BIO-DEGRADABLE ALLOYS

The present invention claims priority from U.S. Provisional Application Nos. 61/143,378, filed on Jan. 8, 2009, 61/168,554, filed on Apr. 10, 2009, and 61/260,363, filed on Nov. 11, 2009, the contents of each of which are expressly incorporated herein by reference.

FIELD OF THE INVENTION

The present invention relates to biodegradable materials useful for manufacturing implantable medical devices, specifically biodegradable compositions comprising metal alloys that can provide high strength when first implanted and are gradually eroded and replaced with body tissue.

BACKGROUND OF THE INVENTION

Medical devices meant for temporary or semi-permanent implant are often made from stainless steel. Stainless steel is strong, has a great deal of load bearing capability, is reasonably inert in the body, does not dissolve in bodily fluids, and is durable, lasting for many years, if not decades. Long lasting medical implants, however, are not always desirable. Many devices for fixing bones become problematic once the bone has healed, requiring removal by means of subsequent surgery. Similarly, short term devices such as tissue staples have to be removed after the tissue has healed, which limits their use internally.

Attempts to generate biodegradable materials have traditionally focused on polymeric compositions. One example is described in U.S. Pat. No. 5,932,459, which is directed to a biodegradable amphiphilic polymer. Another example is described in U.S. Pat. No. 6,368,356, which is directed to biodegradable polymeric hydrogels for use in medical devices. Biodegradable materials for use in bone fixation have been described in U.S. Pat. No. 5,425,769, which is directed to $CaSO_4$ fibrous collagen mixtures. And U.S. Pat. No. 7,268,205 describes the use of biodegradable polyhydroxyalkanoates in making bone fasteners such as screws. However, none of the biodegradable polymeric materials developed to date have demonstrated sufficient strength to perform suitably when substantial loads must be carried by the material, when the material is required to plastically deform during implantation, or when any of the other native characteristic of metal are required from the material. For example, the polyhydroxyalkanoate compositions described in U.S. Pat. No. 7,268,205 do not have sufficient strength on their own to bear weight and must be augmented by temporary fixation of bone segments. In addition, biodegradable polymeric materials tend to lose strength far more quickly than they degrade, because the portions of the material under stress tend to be more reactive, causing preferential dissolution and breakdown at load-bearing regions.

Metals, particularly steels, are thus preferred for the construction of many medical implants. The performance characteristics of steel closely match the mechanical requirements of many load bearing medical devices. Although ordinary steel compounds, unlike stainless steel, will degrade in biological fluids, they are not suitable for use in biodegradable implantable medical devices. This is because ordinary steels do not degrade in a predictable fashion, as one molecule or group of molecules at a time, which can be easily disposed of by the body. Rather, because of their large-grain structures, ordinary steels tend to break down by first degrading at grain boundaries, causing fissures and separations in the medical device, followed by rapid loss of strength and integrity and particulation. Particulation of the medical device is extremely dangerous because it allows small pieces of the device to leave the area of implantation and become lodged in other tissues, where they can cause serious injury including organ failure, heart attack and stroke. The use of ordinary steels in implantable medical devices is also complicated by the fact that ordinary steels typically contain alloying elements that are toxic when released in the body.

There remains a need in the field to develop implantable medical devices that have desirable characteristics associated with steel but are also biodegradable.

SUMMARY OF THE INVENTION

The invention is based, in part, on the discovery that certain metal alloys having, e.g., a fine-grain, substantially austenite structure will biodegrade over time without forming emboli. The invention is also based, in part, on the discovery that certain metal alloys having, e.g., a substantially martensite structure will biodegrade over time without forming emboli. Such alloys are useful for making biodegradable, implantable medical devices.

Accordingly, in one aspect, the invention provides implantable medical devices comprising a biodegradable alloy that dissolves gradually from its exterior surface. In certain embodiments, the rate of dissolution from the exterior surface of the alloy is substantially uniform across smooth portions of the exterior surface (e.g., substantially planar, concave, or convex surfaces). In certain embodiments, the alloy has a fine-grain, substantially austenite structure. In related embodiments, the alloy has a substantially austenite structure that does not preferentially degrade at grain boundaries. In other embodiments, the alloy has a substantially martensite structure.

In certain embodiments, the implantable medical devices comprise an alloy that is substantially austenite in structure and has an average grain size of about 0.5 microns to about 20 microns. For example, in certain embodiments, the average grain size is about 0.5 microns to about 5.0 microns, or about 1.0 micron to about 2.0 microns. In certain embodiments, the implantable medical devices comprise an alloy that is substantially austenite in structure, wherein the surface to volume ratio of individual grains is, on average, greater than $0.1\mu^{-1}$. For example, in certain embodiments, the surface to volume ratio of individual grains is, on average, greater than $1.0\mu^{-1}$.

In certain embodiments, the implantable medical devices comprise an alloy that is an iron alloy (e.g., a steel). For example, in certain embodiments, the alloy contains about 55% to about 80% iron. In certain embodiments, the alloy contains at least two non-iron elements, wherein each of said at least two non-iron elements is present in an amount of at least about 0.5%, and wherein the total amount of said at least two elements makes up greater than about 20% of the alloy. In certain embodiments, greater than about 5% of the alloy consists of elements other than iron, chromium, nickel, and carbon. In certain embodiments, the implantable medical devices comprise an alloy that contains less than about 0.1% nickel. In certain embodiments, the alloy contains less than about 0.1% vanadium. In certain embodiments, the alloy contains less than about 4.0% chromium. In certain embodiments, the alloy contains less than about 6.0% cobalt. In certain embodiments, the alloy contains less than about 0.1% nickel, less than about 0.1% vanadium, less than about 4.0% chromium, and less than about 6.0% cobalt. In certain embodiments, the alloy contains less than about 0.1% of each of the elements in the set consisting of platinum, palladium, iridium, rhodium, rhenium, rubidium, and osmium. In certain embodiments, the alloy contains less than about 0.01% of phosphorus.

In certain embodiments, the implantable medical devices comprise an alloy that comprises an austenite promoting component. In certain embodiments, the amount of austenite promoting component in the alloy is greater than about 10%. In certain embodiments, the austenite promoting component comprises one or more elements selected from the list consisting of manganese, cobalt, platinum, palladium, iridium, aluminum, carbon, nitrogen, and silicon. In certain embodiments, the austenite promoting component comprises one or more elements selected from the list consisting of manganese, cobalt, platinum, palladium, iridium, carbon, and nitrogen, wherein % platinum+% palladium+% iridium+0.5*(% manganese+% cobalt)+30*(% carbon+% nitrogen) is greater than about 12% (e.g., greater than about 14%, about 16%, about 18%, about 19%, or about 20%).

In certain embodiments, the implantable medical devices comprise an alloy comprising a corrosion resisting component. In certain embodiments, the amount of corrosion resisting component in the alloy is less than about 10% (e.g., about 0.5% to about 10%). In certain embodiments, the corrosion resisting component comprises one or more elements selected from the list consisting of chromium, molybdenum, tungsten, tantalum, niobium, titanium, zirconium, and hafnium. In certain embodiments, the corrosion resisting component comprises one or more elements selected from the list consisting of chromium, molybdenum, tungsten, tantalum, niobium, titanium, zirconium, and hafnium, wherein % chromium+% molybdenum+% tungsten+0.5*(% tantalum+% niobium)+2*(% titanium+% zirconium+% hafnium) is about 0.5% to about 7% (e.g., about 6.0%, about 5.5%, about 5.0%, about 4.5%, about 4.0%, about 3.5%, or about 3.0%).

In certain embodiments, the alloy comprises an austenite promoting component and a corrosion resisting component. In certain embodiments, the amount of austenite promoting component in the alloy is greater than about 10% and the amount of corrosion resisting component in the alloy is about 0.5% to about 10%.

In certain embodiments, the implantable medical device is a high tensile bone anchor (e.g., for the repair of separated bone segments). In other embodiments, the implantable medical device is a high tensile bone screw (e.g., for fastening fractured bone segments). In other embodiments, the implantable medical device is a high strength bone immobilization device (e.g., for large bones). In other embodiments, the implantable medical device is a staple for fastening tissue. In other embodiments, the implantable medical device is a craniomaxillofacial reconstruction plate or fastener. In other embodiments, the implantable medical device is a dental implant (e.g., a reconstructive dental implant). In still other embodiments, the implantable medical device is a stent (e.g., for maintaining the lumen of an opening in an organ of a human or animal body).

In certain embodiments, the implantable medical device comprises a geometry that maximizes the surface to mass ratio. For example, in certain embodiments, the implantable medical device comprises one or more openings (e.g., recesses) in the surface of the device or one or more passageways through the device.

In certain embodiments, the implantable medical device further comprises a therapeutic agent. In certain embodiments, the therapeutic agent is coated upon the surface of the device. In other embodiments, the therapeutic agent is incorporated into the body of the device (e.g., into the pores of the alloy from which the implantable medical device was made, into a recess in the surface of the device, or in a passageway through the device).

In certain embodiments, the implantable medical device further comprises a biodegradable gel. In certain embodiments, the biodegradable gel is coated upon the surface of the device. In other embodiments, the biodegradable gel is incorporated into the body of the device (e.g., into the pores of the alloy from which the implantable medical device was made, into a recess in the surface of the device, or in a passageway through the device). In certain embodiments, the biodegradable gel comprises a therapeutic agent.

In another aspect, the invention provides a container containing an implantable medical device of the invention. In certain embodiments, the container further comprises an instruction (e.g., for using the implantable medical device for a medical procedure).

The invention and additional embodiments thereof will be set forth in greater detail in the detailed description that follows.

DETAILED DESCRIPTION OF THE INVENTION

As used herein, the term "percentage" when used to refer to the amount of an element in an alloy means a weight-based percentage. "Weighted percentages" of corrosion resisting and austenite promoting components, however, are calculated in a manner such that the weighted percentages do not necessarily correspond to the actual weight-based percentages.

The object of the present invention is to provide medical devices for temporary implantation in the body of a subject (e.g., a human or animal subject), wherein the devices are made using a biodegradable alloy. The biodegradable alloy is one that is not a stainless steel, but instead undergoes reactions involving normal body chemistry to biodegrade or bioabsorb over time and be removed by normal body processes. It is another object of the invention to provide implantable medical devices made using a biodegradable alloy that is non-toxic and/or non-allergenic as it is degrading and being processed by the body. It is yet another object of the invention to provide implantable medical devices made using a biodegradable alloy that has little or no magnetic susceptibility and does not distort MRI images.

The invention is thus based, in part, on the discovery that certain alloys having, e.g., a fine-grain, substantially austenite structure will biodegrade over time without forming emboli. These austenite alloys exhibit little or no magnetic susceptibility and can be made non-toxic and/or non-allergenic by controlling the amounts of various metals (e.g., chromium and nickel) incorporated into the alloys. The invention is also based, in part, on the discovery that certain alloys having, e.g., a substantially martensite structure will biodegrade over time without forming emboli. These martensite alloys can also be made non-toxic and/or non-allergenic by controlling the amounts of various metals (e.g., chromium and nickel) incorporated into the alloys. The alloys may be incorporated into a variety of implantable medical devices that are used to heal the body of a subject (e.g., a human or other animal), but become unnecessary once the subject is healed. The alloys can be used, for example, to make biodegradable, implantable medical devices that require high strength, such as bone fasteners for weight-bearing bones. The alloys can also be used to make biodegradable, implantable medical devices that require ductility, such as surgical staples for tissue fixation.

Accordingly, in one aspect, the invention provides implantable medical devices comprising a biodegradable alloy that dissolves from its exterior surface. As used herein, the term "alloy" means a mixture of chemical elements comprising two or more metallic elements. Biodegradable alloys suitable for making implantable medical devices of the invention can be, for example, iron alloys (e.g., steels). In certain embodiments, the iron alloys comprise about 55% to about 65%, about 57.5% to about 67.5%, about 60% to about 70%, about 62.5% to about 72.5%, about 65% to about 75%, about 67.5% to about 77.5%, about 70% to about 80%, about 72.5% to about 82.5%, or about 75% to about 85% iron. The iron alloys further comprise one or more non-iron metallic elements. The one or more non-iron metallic elements can include, for example, transition metals, such as manganese, cobalt, nickel, chromium, molybdenum, tungsten, tantalum, niobium, titanium, zirconium, hafnium, platinum, palladium, iridium, rhenium, osmium, rhodium, etc., or non-transition metals, such as aluminum. In certain embodiments, the iron alloys comprise at least two non-iron metallic elements. The at least two non-iron elements can be present in an amount of at least about 0.5% (e.g., at least about 1.0%, about 1.5%, about 2.0%, about 2.5%, about 3.0%, about 4.0%, about 5.0%, or more). In certain embodiments, the iron alloys comprise at least two non-iron metallic elements, wherein each of said at least two non-iron elements is present in an amount of at least about 0.5%, and wherein the total amount of said at least two elements is at least about 15% (e.g., at least about 17.5%, about 20%, about 22.5%, about 25%, about 27.5%, about 30%, about 32.5%, about 35%, about 37.5%, or about 40%). The biodegradable alloys can also comprise one or more non-metallic elements. Suitable non-metallic elements include, for example, carbon, nitrogen, and silicon. In certain embodiments, the iron alloys comprise at least about 0.01% (e.g., about 0.01% to about 0.10%, about 0.05% to about 0.15%, about 0.10% to about 0.20%, about 0.15% to about 0.25%, or about 0.20% to about 0.30%) of at least one non-metallic element.

Biodegradable alloys suitable for use in the implantable medical devices of the invention are designed to degrade from the outside inward, such that they maintain their strength for a greater portion of their life and do not particulate or embolize. Without intending to be bound by theory, it is believed that this is accomplished by providing an alloy structure that either has no appreciable reactive grain boundaries, forcing degradation to take place at the surface molecular layer, or by providing a very fine grain alloy that acts as a homogeneous, grain free material. In certain embodiments, the rate of dissolution from an exterior surface of a suitable biodegradable alloy is substantially uniform at each point of the exterior surface. As used herein in this context, "substantially uniform" means that the rate of dissolution from a particular point on an exterior surface is +/−10% of the rate of dissolution at any other point on the same exterior surface. As persons skilled in the art will appreciate, the type of "exterior surface" contemplated in these embodiments is one that is smooth and continuous (i.e., substantially planar, concave, convex, or the like) and does not include sharp edges or similar such discontinuities, as those are locations where the rate of dissolution is likely to be much higher. A "substantially" planar, concave, or convex surface is a surface that is planar, concave, convex, or the like and does not contain any bumps, ridges, or grooves that rise above or sink below the surface by more than 0.5 mm.

Steel alloys have iron as their primary constituent. Depending upon a combination of (i) the elements alloyed with the iron and (ii) the historical working of the alloy, steels can have different structural forms, such as ferrite, austenite, martensite, cementite, pearlite, and bainite. In some instances, steels having the same composition can have different structures. For example, martensite steel is a form of high tensile steel that can be derived from austenite steel. By heating austenite steel to between 1750° F. and 1950° F., and then rapidly cooling it to below the martensite transition temperature, the face centered cubic structure of the austenite steel will reorient into a body centered tetragonal martensite structure, and the martensite structure will freeze into place. Martensite steel does not have appreciable grain boundaries, and thus provides no primary dissolution path to the interior of the steel. The result is a slow dissolution from the outside, without the formation of emboli. Metallurgical examination of martensitic material will show "pre-austenitic grain boundaries," places where the austenite grain boundaries once existed, but these are nonreactive traces of the former structure.

Accordingly, in certain embodiments, the biodegradable implantable medical devices of the invention comprise an alloy (e.g., an iron alloy) having a substantially martensite structure. As used herein, the term "substantially martensite structure" means an alloy having at least 90% martensite structure. In certain embodiments, the alloy has at least 91%, 92%, 93%, 94%, 95%, 96%, 97%, 98%, 99%, 99.5%, 99.8%, 99.9% or more martensite structure.

The martensite alloy can have the composition of any alloy described herein. For example, in certain embodiments, the martensite alloy is formed from an austenite alloy described herein. In certain embodiments, the martensite alloy comprises carbon, chromium, nickel, molybdenum, cobalt, or a combination thereof. For example, in certain embodiments, the martensite alloy comprises (i) carbon, (ii) chromium and/or molybdenum, and (iii) nickel and/or cobalt. In certain embodiments, the martensite alloy comprises about 0.01% to about 0.15%, about 0.05% to about 0.20%, about 0.10% to about 0.25%, about 0.01% to about 0.05%, about 0.05% to about 0.10%, about 0.10% to about 0.15%, or about 0.15% to about 0.20% carbon. In certain embodiments, the martensite alloy comprises about 0.1% to about 6.0%, about 1.0% to about 3.0%, about 2.0% to about 4.0%, about 3.0% to about 5.0%, or about 4.0% to about 6.0% chromium. In certain embodiments, the martensite alloy comprises about 0.1% to about 6.0%, about 0.5% to about 2.5%, about 1.0% to about 3.0%, about 1.5% to about 3.5%, about 2.0% to about 4.0%, about 2.5% to about 4.5%, about 3.0% to about 5.0%, about 3.5% to about 5.5%, or about 4.0% to about 6.0% molybdenum. In certain embodiments, the martensite alloy comprises about 5.0% to about 9%, about 6.0% to about 10%, about 7.0% to about 11%, about 8.0% to about 12%, about 9.0% to about 13%, about 10% to about 14%, or about 11% to about 15% nickel. In certain embodiments, the martensite alloy comprises about 5.0% to about 10%, about 7.5% to about 12.5%, about 10% to about 15%, about 12.5% to about 17.5%, or about 15% to about 20% cobalt.

In certain embodiments, the martensite alloy contains about 2.0% to about 6.0%, about 3.0% to about 7.0%, about 3.5% to about 7.5%, about 4.0% to about 8.0%, about 4.5% to about 8.5%, or about 5.0% to about 9.0% of a corrosion resisting component. In certain embodiments, the martensite alloy contains about 2.5%, about 3.0%, about 3.5%, about 4.0%, about 4.5%, about 5.0%, about 5.5%, or about 6.0% of a corrosion resisting component. In certain embodiments, the corrosion resisting component is calculated as a sum of the percentages of corrosion resisting elements (e.g., chromium, molybdenum, tungsten, tantalum, niobium, titanium, zirconium, hafnium, etc.) in the alloy. In other embodiments, the corrosion resisting component is calculated as a weighted sum of the corrosion resisting elements in the alloy. In certain embodiments, individual elements in the weighted sum are weighted according to their corrosion resisting efficacy, as compared to chromium. In certain embodiments, the weighted % corrosion resisting component is determined according to the formula: % chromium+% molybdenum+% tungsten+0.5*(% tantalum+% niobium)+2*(% titanium+% zirconium+% hafnium).

In certain embodiments, the martensite alloy contains at least about 10%, about 15%, about 18%, about 20%, about 22%, or about 24% of a austenite promoting component. For example, in certain embodiments, the martensite alloy contains about 10% to about 20%, about 15% to about 25%, about 20% to about 30%, about 25% to about 35%, about 30% to about 40% of an austenite promoting component. In certain embodiments, the martensite alloy comprises about 22%, about 23%, about 24%, about 25%, about 26%, about 27%, or about 28% of an austenite promoting component. In certain embodiments, the austenite promoting component is calculated as a sum of the percentages of austenite promoting elements (e.g., nickel, manganese, cobalt, platinum, palladium, iridium, aluminum, carbon, nitrogen, silicon, etc.) in the alloy. In other embodiments, the austenite promoting component is calculated as a weighted sum of all the austenite promoting elements in the alloy. In certain embodiments, individual elements in the weighted sum are weighted according to their austenite promoting efficacy, as compared to nickel. In certain embodiments, the weighted % austenite promoting component is calculated according to the formula: % nickel+% platinum+% palladium+% iridium+0.5*(% manganese+% cobalt)+30*(% carbon+% nitrogen).

In certain embodiments, the martensite alloy comprises about 2.0% to about 4.0%, about 3.0% to about 5.0%, or about 4.0% to about 6.0% of a corrosion resisting component, and about 10% to about 20%, about 15% to about 25%, about 20% to about 30%, about 25% to about 35%, or about 30% to about 40% of an austenite promoting component. For example, in certain embodiments, the martensite alloy comprises about 3.0% to about 5.0% of a corrosion resisting component and about 20% to about 30% of an austenite promoting component. In certain embodiments, the corrosion resisting and austenite promoting components are calculated as sums of the percentages of corrosion resisting and austenite promoting elements, respectively. In other embodiments, the corrosion resisting and austenite promoting components are calculated as weighted sums of the corrosion resisting and austenite promoting elements, respectively.

While martensite alloys have the desirable characteristic of lacking grain boundaries, austenite alloys are particularly useful for medical implants because of their low magnetic susceptibility, which can be useful where the alloy is exposed to a strong magnetic field. It is desirable for medical implants to have low magnetic susceptibility because they may be used in patients that would have future need of Magnetic Resonance Imaging (MRI), which utilizes very high magnetic fields. A magnetic reactive alloy in a strong magnetic field can experience heating, causing local tissue stress and damage to tissue surrounding the implant. Magnetic reactive implants also distort MRI images, making them unreadable. In addition, austenite alloys can provide certain mechanical benefits, since they undergo larger plastic deformations between their elastic limit (yield point) and ultimate failure, as compared to martensite alloys. For example, whereas a martensite alloy may have a maximum elongation of about 16% to 20%, an austenite alloy can have a maximum elongation of about 50% to 60%.

Thus, in certain embodiments, the biodegradable implantable medical devices of the invention comprise an alloy (e.g., an iron alloy) having a substantially austenite structure. As used herein, the term "substantially austenite structure" means at least 85% austenite structure. In certain embodiments, the alloy has at least 88%, 90%, 91%, 92%, 93%, 94%, 95%, 96%, 97%, 98%, 99%, 99.5%, 99.8%, 99.9% or more austenite structure. In certain embodiments, the austenite alloy has substantially no martensite or ferrite structure. As used herein, the term "substantially no martensite or ferrite structure" means less than 5% (e.g., less than 4%, 3%, 2%, 1%, 0.5%, 0.2%, 0.1%, or 0.05%) martensite or ferrite structure. In certain embodiments, the austenite alloy is characterized by a maximum elongation of about 40% to about 65% (e.g., about 50% to about 60%).

Austenitic steels have grains with defined boundaries of irregular shape. Since austenite is a face centered cubic structure, the grains tend to be cubic when viewed perpendicular to a major lattice plane. In austenite alloys having either very low carbon or very low chromium, it is possible to create a structure with a fine grain size (e.g., about 0.5 to about 5.0 microns on a side). A cubic austenite grain of 2.5 microns has a total surface area of 37.5 square microns and a volume of 15.625 cubic microns, for a surface to volume ratio of $2.4\mu^{-1}$ and a total mass of 0.12 micrograms. Because of the extremely small mass of the grain, the grain material reacts as quickly as the grain boundary material when placed in a biological environment, allowing the alloy to shed material from the outside. This, in turn, prevents weakening of the material bulk along grain boundaries and grain separation from the material bulk of the alloy. As the size of grains increase, however, the ratio of surface to volume decreases. Each grain becomes bigger, taking longer to be absorbed, making it more likely that dissolution will take place along grain boundaries, penetrating deeper into the alloy's material bulk and thereby reducing the strength of the alloy.

Accordingly, the rate of biodegradation of austenite alloys can be altered by controlling the grain size and surface to volume ratio of the individual grains. As the grain size increases, with a commensurate decrease in the surface-to-volume ratio, biodegradation progresses faster toward the center of the device, increasing the total biodegradation rate. However, too large a grain size can cause separation of grains and adverse effects.

In certain embodiments, the austenite alloy has an average grain size of about 0.5 microns to about 20 microns on each side. For example, in certain embodiments, the average grain size is about 0.5 microns to about 5.0 microns, about 2.5 microns to about 7.5 microns, about 5.0 microns to about 10 microns, about 7.5 microns to about 12.5 microns, about 10 microns to about 15 microns, about 12.5 microns to about 17.5 microns, or about 15 microns to about 20 microns on each side. In certain embodiments, the average grain size is about 0.5 to about 3.0 microns, or about 1.0 micron to about 2.0 microns on each side. In certain embodiments, the austenite alloy has a structure wherein the surface to volume ratio of individual grains is, on average, greater than $0.1\mu^{-1}$. For example, in certain embodiments, the surface to volume ratio of individual grains is, on average, greater than $0.2\mu^{-1}$, $0.3\mu^{-1}$, $0.4\mu^{-1}$, $0.5\mu^{-1}$, $0.6\mu^{-1}$, $0.7\mu^{-1}$, $0.8\mu^{-1}$, $0.9\mu^{-1}$, $1.0\mu^{-1}$, $1.5\mu^{-1}$, $2.0\mu^{-1}$, $2.5\mu^{-1}$, $3.0\mu^{-1}$, $3.5\mu^{-1}$, $4.0\mu^{-1}$, $4.5\mu^{-1}$, $5.0\mu^{-1}$, $6.0\mu^{-1}$, $7.0\mu^{-1}$, $8.0\mu^{-1}$, $9.0\mu^{-1}$, $10.0\mu^{-1}$, $11.0\mu^{-1}$, $12.0\mu^{-1}$, $13.0\mu^{-1}$, $14.0\mu^{-1}$, $15.0\mu^{-1}$, or more.

Austenite grain sizes of about 0.5 microns to about 20 microns can be achieved by successive cycles of mechanical working to break down the alloy, followed by thermal recrystallization. The mechanical working of materials, whether done at cold temperatures (i.e. room temperature to 200° C.) or at elevated temperatures, causes strain-induced disruption of the crystal structure, by physically forcing the alloy into a new shape. The most common method of mechanical working of metals is by reducing the thickness of a sheet of metal between two high pressure rolls, causing the exiting material to be substantially thinner (e.g., 20%-60% thinner) than the original thickness. Other methods such as drawing can also be employed. The process of mechanically working metals breaks down larger, contiguous lattice units into different structures. More importantly, it stores substantial strain-induced energy into distorted lattice members, by straining lattice structure distances to higher energy arrangements. Subsequent low-temperature recrystallization, which takes place at about 0.35 to about 0.55 times the absolute melting temperature of the alloy, allows the lattice structure to undergo rearrangements to a lower energy condition, without changes to overall macro dimensions. To accommodate lattice rearrangement without gross changes in dimensions, the size of individual lattice sub-units, or grains, is reduced, releasing substantial strain energy by breaking the lattice into smaller sub-units, and producing a finer grain structure. The process of mechanical working followed by recrystallization can be repeated serially, producing finer and finer grains.

In certain embodiments, the austenite alloy comprises carbon. For example, in certain embodiments, the alloy comprises about 0.01% to about 0.10%, about 0.02% to about 0.12%, about 0.05% to about 0.15%, about 0.07% to about 0.17%, about 0.10% to about 0.20%, about 0.12% to about 0.22%, or about 0.15% to about 0.25% carbon. In certain embodiments, the austenite alloy comprises one or more (e.g., two or more) elements selected from the list consisting of nickel, cobalt, aluminum, and manganese. In certain embodiments, the alloy comprises about 2.0% to about 6.0%, about 3.0% to about 7.0%, about 4.0% to about 8.0%, or about 5.0% to about 9.0% nickel. In other embodiments, the alloy comprises substantially no nickel. In certain embodiments, the alloy comprises about 10% to about 20%, about 15% to about 20%, about 15% to about 25%, about 18% to about 23%, about 20% to about 25%, or about 20% to about 30% cobalt. In certain embodiments, the alloy comprises less than about 5.0% (e.g., less than about 4.5%, about 4.0%, about 3.5%, about 3.0%, or about 2.5%) manganese. In certain embodiments, the alloy comprises about 0.5% to about 1.5%, about 1.0% to about 2.0%, or about 1.5% to about 2.5% manganese. In other embodiments, the alloy comprises about 1.0% to about 8.0%, about 6.0% to about 10%, about 8.0% to about 12%, or about 10% to about 14% manganese. In certain embodiments, the austenite alloy comprises one or more (e.g., two or more) elements selected from the list consisting of chromium, molybdenum, and tantalum. In certain embodiments, the alloy comprises about 0.5% to about 1.5%, about 1.0% to about 2.0%, about 1.5% to about 2.5%, or about 2.0% to about 3.0% chromium. In other embodiments, the alloy comprises substantially no chromium. In certain embodiments, the alloy comprises about 0.5% to about 1.5%, about 1.0% to about 2.0%, about 1.5% to about 2.5%, or about 2.0% to about 3.0% molybdenum. In certain embodiments, the alloy comprises about 1.0% to about 3.0%, about 2.0% to about 4.0%, about 3.0% to about 5.0%, or about 4.0% to about 6.0% tantalum. In certain embodiments, the austenite alloy comprises (i) carbon, (ii) at least two elements selected from the list consisting of nickel, cobalt, aluminum, and manganese, and (iii) at least two elements selected from the list consisting of chromium, molybdenum, and tantalum.

Aside from the pattern of dissolution, the rate of dissolution and the release of potentially toxic elements need to be controlled in alloys used to make implantable medical devices of the invention. The particular elements used to make up an alloy help determine the physical and chemical properties of the resulting alloy. For example, adding small amounts of carbon to iron changes the structure of the iron, creating steel that is greatly increased in hardness and strength, while changing the plasticity relative to iron. Similarly, stainless steels are fabricated by adding elements to the iron that decrease corrosion (i.e., corrosion resisting components), such as chromium and molybdenum. A stainless steel that resists corrosion in a biological system can contain, for example, 18% chromium and 1% molybdenum. Titanium, niobium, tantalum, vanadium, tungsten, zirconium, and hafnium likewise provide a protective effect that slows down the rate of degradation of steel in a biologic system.

A stainless steel that does not break down in the intended biological system is typically not suitable for use in a biodegradable implant. Thus, alloys having large quantities of corrosion resisting elements, such as chromium, molybdenum, titanium, and tantalum, usually cannot be used to make biodegradable implantable medical devices of the invention. However, small quantities of such corrosion resisting elements are useful for controlling the biodegradation rate of suitable alloys. Accordingly, in certain embodiments, an alloy useful for making a biodegradable implantable medical device of the invention (e.g., an austenite alloy) contains at least about 0.5%, about 1.0%, about 1.5%, about 2.0%, about 2.5%, about 3.0%, or about 3.5%, but less than about 15%, about 12%, about 11%, about 10%, about 9.0%, about 8.0% or about 7.0% of a corrosion resisting component. For example, in certain embodiments, the alloy contains about 1.0% to about 7.0%, about 2.0% to about 8.0%, or about 3.0% to about 9.0% of a corrosion resisting component. In certain embodiments, the alloy (e.g., austenite alloy) contains about 3.0%, about 3.5%, about 4.0%, about 4.5%, about 5.0%, about 5.5%, about 6.0%, about 6.5%, or about 7.0% of a corrosion resisting component. In certain embodiments, the corrosion resisting component is calculated as a sum of the percentages of corrosion resisting elements (e.g., chromium, molybdenum, tungsten, tantalum, niobium, titanium, zirconium, hafnium, etc.) in the alloy. In other embodiments, the corrosion resisting component is a weighted sum of all the corrosion resisting elements in the alloy. For example, in certain embodiments, individual elements in the weighted sum are weighted according to their corrosion resisting efficacy, as compared to chromium. In certain embodiments, the weighted % corrosion resisting component is determined according to the formula: % chromium+% molybdenum+% tungsten+0.5*(% tantalum+% niobium)+2*(% titanium+% zirconium+% hafnium).

Corrosion resisting elements, such as chromium and molybdenum, are ferrite promoting and tend to cause steel to form a ferritic structure. To overcome such ferrite promotion and achieve an austenite structure, austenite promoting elements can be added to the alloy. Austenite promoting elements include, for example, nickel, manganese, cobalt, platinum, palladium, iridium, aluminum, carbon, nitrogen, and silicon. Accordingly, in certain embodiments, an alloy (e.g., an austenite alloy) useful for making an implantable medical device of the invention contains an austenite promoting component. In certain embodiments, the alloy contains about 10% to about 20%, about 15% to about 25%, about 20% to about 30%, about 25% to about 35%, or about 30% to about 40% of an austenite promoting component. In certain embodiments, the alloy contains at least about 10%, about 12%, about 14%, about 16%, about 18%, about 20%, about 22%, about 24%, about 26%, about 28%, or about 30% of an austenite promoting component. In certain embodiments, the austenite promoting component is calculated as a sum of the percentages of austenite promoting elements (e.g., nickel, cobalt, manganese, platinum, palladium, iridium, aluminum, carbon, nitrogen, silicon, etc.) in the alloy. In other embodiments, the austenite promoting component is a weighted sum of the austenite promoting elements in the alloy. In certain embodiments, individual elements in the weighted sum are weighted according to their austenite promoting efficacy, as compared to nickel. In certain embodiments, the weighted % austenite promoting component is calculated according to the formula: % nickel+% platinum+% palladium+% iridium+0.5*(% manganese+% cobalt)+30*(% carbon+% nitrogen). In certain embodiments, the alloy contains a weighted % austenite promoting component of about 15% to about 25% (e.g., about 16%, about 17%, about 18%, about 19%, about 20%, about 21%, about 22%, about 23%, about 24%, or about 25%). In certain embodiments, the alloy contains an unweighted % austenite promoting component of about 25% to about 35% (e.g., about 28%, about 29%, about 30%, about 31%, about 32%, about 33%, about 34%, or about 35%).

In certain embodiments, an alloy (e.g., an austenite alloy) useful for making an implantable medical device of the invention contains less than about 5.0% (e.g., about 0.1% to about 2.5%, about 0.5% to about 3.0%, about 1.0% to about 3.5%, about 1.5% to about 4.0%, or about 2.0% to about 4.5%) of platinum, iridium, and osmium, either individually or in total. In certain embodiments, the alloy contains substantially no platinum, palladium, or iridium. As used herein, "substantially no" platinum, palladium, or iridium means that the alloy contains less than 0.1% of platinum, palladium, or iridium. In certain embodiments, the alloy contains substantially none platinum, palladium, and iridium. In certain embodiments, the alloys contain less than about 0.05%, or about 0.01% of each of platinum, palladium, or iridium. In certain embodiments, the alloys contain less than about 0.05%, or less than about 0.01%, of each of platinum, palladium, and iridium. In other embodiments, the total amount of platinum, iridium, and osmium in the alloy is about 5.0% or greater, and the alloy further comprises at least one additional metal element other than iron, manganese, platinum, iridium, and osmium (e.g., at least about 0.5% or more of said at least one additional metal element). In certain embodiments, the at least one addition metal element is a corrosion resisting element (e.g., chromium, molybdenum, tungsten, titanium, tantalum, niobium, zirconium, or hafnium) or a austenite promoting element selected from the group consisting of nickel, cobalt, and aluminum.

Biodegradable alloys implanted in a human or animal body need to be relatively non-toxic because all of the elements in the alloys will eventually be dissolved into body fluids. Nickel is often used to stabilize an austenitic crystal structure. However, many people have nickel allergies and cannot tolerate nickel ions in their systems. Having nickel as part of a biodegradable alloy guarantees that all of the nickel in the alloy will eventually be absorbed by the host's body, which can cause complications in a nickel sensitive individual. Likewise, chromium, cobalt, and vanadium have some toxicity in the human body, and should be minimized in a biodegradable alloy. Accordingly, in certain embodiments, an alloy useful for making a biodegradable implantable medical device of the invention (e.g., an austenite alloy) contains less than about 9.0%, about 8.0%, about 7.0%, about 6.0%, about 5.0%, about 4.0%, about 3.0%, about 2.5%, about 2.0%, about 1.5%, about 1.0%, or about 0.5% of each of nickel, vanadium, chromium, and cobalt. In certain embodiments, the alloy contains substantially no nickel. As used here, the phrase "substantially no nickel" means that the alloy contains 0.1% or less nickel. In certain embodiments, the alloy contains less than about 0.05%, less than about 0.02%, or less than about 0.01% nickel. In certain embodiments, the alloy contains substantially no vanadium. As used here, the phrase "substantially no vanadium" means that the alloy contains 0.1% or less vanadium. In certain embodiments, the alloy contains less than about 0.05%, less than about 0.02%, or less than about 0.01% vanadium. In certain embodiments, the alloy contains less than about 4.0% chromium (e.g., less than about 3.0%, about 2.0%, or about 1.5%). In certain embodiments, the alloy contains substantially no chromium. As used here, the phrase "substantially no" chromium means that the alloy contains 0.1% or less chromium. In certain embodiments, the alloy contains less than about 0.05%, less than about 0.02%, or less than about 0.01% chromium. In certain embodiments, the alloy contains less than about 6.0% (e.g., less than about 5.0%, about 4.0%, about 3.0%, about 2.0%, or about 1.0%) cobalt.

To remove or minimize toxic elements from the alloys used to created the biodegradable implantable medical devices of the invention, the toxic elements can be replaced with non-toxic counterparts. For example, since nickel is used as an austenite promoting element, it can be replaced with other austenite promoting elements, such as manganese, cobalt, platinum, palladium, iridium, aluminum, carbon, nitrogen, and silicon. Similarly, since chromium is used as a corrosion resisting element, it can be replaced with other corrosion resisting elements, such as molybdenum, tungsten, titanium, tantalum, niobium, zirconium, and hafnium. However, not all alloy substitutions are equivalent. For a corrosion resisting effect, molybdenum is as effective as chromium, while niobium and tantalum are only half as effective as chromium, and titanium is twice as effective as chromium. For austenite promoting effect, manganese and cobalt are only half as effective as nickel, while carbon is 30 times more effective than nickel, and nitrogen is 25-30 times more effective than nickel. Accordingly, in certain embodiments, a biodegradable alloy is rendered non-allergenic or less allergenic by replacing one part of nickel with two parts manganese, one part of manganese and one part of cobalt, or two parts of cobalt. In other embodiments, a biodegradable alloy is rendered non-toxic or less toxic by replacing one part of chromium with one part of molybdenum, half a part of titanium, or two parts of tantalum or niobium. In certain embodiments, the total percentage of nickel, cobalt and manganese is from about 10% to about 20%, about 15% to about 25%, or about 20% to about 30%, about 25% to about 35%, or about 30% to about 40%, wherein the percentage of nickel is less than about 9.0%, about 8.0%, about 7.0%, about 6.0%, about 5.0%, about 4.0%, or about 3.0%. In other embodiments, the total percentage of chromium and molybdenum is from about 1.0% to about 7.0%, about 2.0% to about 8.0%, about 3.0% to about 9.0%, or about 4.0% to about 10%, wherein the amount of chromium is less than about 2.0%, about 1.5%, about 1.0%, or about 0.5%.

Additional elements that can be included in alloys useful for making biodegradable, implantable medical devices of the invention include rhodium, rhenium, and osmium. In certain embodiments, the amount of rhodium, rhenium, or osmium in the alloy is less that about 5.0% (e.g., about 0.1% to about 2.5%, about 0.5% to about 3.0%, about 1.0% to about 3.5%, about 1.5% to about 4.0%, or about 2.0% to about 4.5%). In certain embodiments, there is substantially no rhodium, rhenium, or osmium in the alloy. As used herein, "substantially no" rhodium, rhenium, or osmium means that the alloy contains less than about 0.1% of rhodium, rhenium, or osmium. In certain embodiments, there is substantially none rhodium, rhenium, and osmium in the alloy. In certain embodiments, the alloy contains less than about 0.05%, or less than about 0.01%, of rhodium, rhenium, or osmium. In certain embodiments, the alloy contains less than about 0.05%, or less than about 0.01%, of each of rhodium, rhenium, and osmium.

In certain embodiments, when one or more elements selected from the group consisting of platinum, palladium, iridium, rhodium, rhenium, and osmium is present in an alloy useful for making biodegradable, implantable medical devices of the invention, the amount of manganese in the alloy is less than about 5.0% (e.g., less than about 4.5%, about 4.0%, about 3.5%, about 3.0%, or about 2.5%). In other embodiments, when one or more elements selected from the group consisting of platinum, palladium, iridium, rhenium, rubidium, and osmium is present in the alloy and the amount of manganese in the alloy is about 5.0% or greater (e.g., about 5.0% to about 30%), then the alloy further comprises at least one additional metal element. In certain embodiments, the at least one addition metal element is a corrosion resisting element (e.g., chromium, molybdenum, tungsten, titanium, tantalum, niobium, zirconium, or hafnium) or a austenite promoting element selected from the group consisting of nickel, cobalt, and aluminum.

In certain embodiments, alloys useful for making biodegradable, implantable medical devices of the invention contain substantially no rubidium or phosphorus. As used herein, "substantially no" rubidium or phosphorus means less than 0.1% of rubidium of phosphorus. In certain embodiments, the alloys contain substantially none rubidium and phosphorus. In certain embodiments, the alloys contain less than about 0.05%, or less than about 0.01%, of rubidium or phosphorus. In certain embodiments, the alloys contain less than about 0.05%, or less than about 0.01%, of each of rubidium and phosphorus.

In certain embodiments, the present invention provides biodegradable implantable medical devices comprising a range of biodegradable alloys (e.g., austenitic alloys) that are acceptably non-allergenic, non-toxic, have little or no magnetic susceptibility, and provide a useful range of degradation rates. The following are exemplary boundaries defining alloys useful in the biodegradable implantable medical devices of the present invention:

substantially no nickel;
substantially no vanadium;
less than about 6.0% chromium;
less than about 10% cobalt;
a corrosion resisting component of less than about 10% (e.g., about 0.5% to about 10%); and
an austenite promoting component of at least about 10% (e.g., about 10% to about 40%).

In certain embodiments, the alloys contain about 55% to about 80% iron. For example, in certain embodiments, the alloys contain about 55% to about 65%, about 60% to about 70%, about 65% to about 75%, about 70% to about 80% iron. In certain embodiments, the amount of chromium is less than about 4.0% and the amount of cobalt is less than about 6.0%. In certain embodiments, the amount of chromium is less than about 2.0% and the amount of cobalt is less than about 4.0%. In certain embodiments, the corrosion resisting component is less than about 8.0% (e.g., about 0.5% to about 8.0%) and the austenite promoting component is greater than about 12%. In certain embodiments, the corrosion resisting component is less than less than about 7.0% (e.g., about 0.5% to about 7.0%) and the austenite promoting component is greater than about 14%. In certain embodiments, the corrosion resisting component is less than about 6.0% (e.g., about 0.5% to about 6.0%) and the austenite promoting component is greater than about 16%. In certain embodiments, the corrosion resisting and austenite promoting components are calculated as sums of the percentages of corrosion resisting and austenite promoting elements, respectively. In other embodiments, the corrosion resisting and austenite promoting components are calculated as weighted sums of the corrosion resisting and austenite promoting elements, respectively. In certain embodiments, the weighted % corrosion resisting component is determined according to the formula: % chromium+% molybdenum+% tungsten+0.5*(% tantalum+% niobium)+ 2*(% titanium+% zirconium+% hafnium). In certain embodiments, the weighted % austenite promoting component is calculated according to the formula: % nickel+% platinum+% palladium+% iridium+0.5*(% manganese+% cobalt)+30*(% carbon+% nitrogen). In certain embodiments, the alloys contain less than about 5.0% manganese (e.g., less than about 4.5%, about 4.0%, about 3.5%, about 3.0%, or about 2.5%). In certain embodiments, the alloys contain one or more elements selected from the group consisting of platinum, palladium, iridium, rhodium, rhenium, and osmium. In certain embodiments, the alloys contain about 0.5% to about 5.0% of one or more elements selected from the group consisting of platinum, palladium, iridium, rhodium, rhenium, and osmium. In certain embodiments, the alloys contain substantially none of the elements selected from the group consisting of platinum, palladium, iridium, rhodium, rhenium, and osmium. In certain embodiments, the alloys contain substantially none of the elements selected from the group consisting of rubidium and phosphorus.

The degradation of an entire implant is a function of the mass of the implant as compared to its surface area. Implants come in many different sizes and shapes. A typical coronary stent, for example, weighs 0.0186 grams and has a surface area of 0.1584 square-inches. At a degradation rate of 1 mg/square-inch/day, a coronary stent would loose 50% of its mass in 30 days. In comparison, a 12 mm long cannulated bone screw weighs 0.5235 g and has a surface area of 0.6565 square-inches. At the same degradation rate of 1 mg/square-inch/day, the cannulated screw will loose half of its mass in 363 days. Thus, as persons skilled in the art will readily appreciate, it is desirable to have biodegradable alloys that have a range of degradation rates to accommodate the variety of implants used in the body of a subject.

In addition, the biodegradation rate of the implantable medical devices of the present invention are significantly influenced by the transport characteristics of the surrounding tissue. For example, the biodegradation rate of an implant placed into bone, where transport to the rest of the body is limited by the lack of fluid flow, would be slower than a vascular stent device that is exposed to flowing blood. Similarly, a biodegradable device embedded in tissue would have slower degradation rate than a device exposed to flowing blood, albeit a faster degradation rate than if the device was embedded in bone. Moreover, different ends of a medical device could experience different rates of degradation if, for example, one end is located in bone and the other end is located in tissue or blood. Modulation of biodegradation rates based on the location of the device and ultimate device requirements is thus desirable.

In order to control the dissolution rate of a medical device independent of the geometric shape changes that occur as the device degrades, several techniques have been developed. The first method to alter the dissolution profile of a metallic device is to alter the geometry of the device such that large changes in surface area are neutralized. For example, the surface to mass ratio can be increased or maximized. A substantially cylindrical device, which would lose surface area linearly with the loss of diameter as the device degrades, could have a concentric hole drilled through the center of the device. The resulting cavity would cause a compensating increase in surface area as alloy was dissolved from the luminal surface of the device. As a result, the change in surface area as the device degrades over time—and thus the change in rate of degradation—would be minimize or eliminated. A similar strategy of creating a luminal space (e.g., a luminal space that has a shape similar to the outer surface of the device) could be implemented with essentially any type of medical device.

Because biodegradation rates are partially a function of exposure to bodily fluid flow, biodegradation rates can be modified by coating (e.g., all or part of) the biodegradable implantable medical device with a substance that protects the alloy surface. For example, biodegradable hydrogels, such as disclosed in U.S. Pat. No. 6,368,356, could be used to retard exposure of any parts of a device exposed to mobile bodily fluids, thereby retard dissolution and transport of metal ions away from the device. Alternatively, medical devices can be constructed with two or more different alloys described herein, wherein parts of the device that are exposed to mobile bodily fluids are made from more corrosion resistant alloys (i.e., alloys comprising higher amounts of a corrosion resisting component), while parts of the device imbedded in bone or tissue are made from less corrosion resistant alloys. In certain embodiments, the different parts of the device can be made entirely from different alloys. In other embodiments, parts of the device exposed to mobile bodily fluids can have a thin layer or coating of an alloy that is more corrosion resistant than the alloy used to make the bulk of the device.

It is frequently desirable to incorporate bioactive agents (e.g., drugs) on implantable medical devices. For example, U.S. Pat. No. 6,649,631 claims a drug for the promotion of bone growth which can be used with orthopedic implants. Bioactive agents may be incorporated directly on the surface of an implantable medical device of the invention. For example, the agents can be mixed with a polymeric coating, such as a hydrogel of U.S. Pat. No. 6,368,356, and the polymeric coating can be applied to the surface of the device. Alternatively, the bioactive agents can be loaded into cavities or pores in the medical devices which act as depots such that the agents are slowly released over time. The pores can be on the surface of the medical devices, allowing for relatively quick release of the drugs, or part of the gross structure of the alloy used to make the medical device, such that bioactive agents are released gradually during most or all of the useful life of the device. The bioactive agents can be, e.g., peptides, nucleic acids, hormones, chemical drugs, or other biological agents, useful for enhancing the healing process.

As persons skilled in the art will readily recognize, there are a wide array of implantable medical devices that can be made using the alloys disclosed herein. In certain embodiments, the implantable medical device is a high tensile bone anchor (e.g., for the repair of separated bone segments). In other embodiments, the implantable medical device is a high tensile bone screw (e.g., for fastening fractured bone segments). In other embodiments, the implantable medical device is a high strength bone immobilization device (e.g., for large bones). In other embodiments, the implantable medical device is a staple for fastening tissue. In other embodiments, the implantable medical device is a craniomaxillofacial reconstruction plate or fastener. In other embodiments, the implantable medical device is a dental implant (e.g., a reconstructive dental implant). In still other embodiments, the implantable medical device is a stent (e.g., for maintaining the lumen of an opening in an organ of an animal body).

Powdered metal technologies are well known to the medical device community. Bone fasteners having complex shapes are fabricated by high pressure molding of a powdered metal in a carrier, followed by high temperature sintering to bind the metal particles together and remove the residual carrier. Powdered metal devices are typically fabricated from nonreactive metals such as 316LS stainless steel. The porosity of the finished device is partially a function of the metal particle size used to fabricate the part. Because the metal particles are much larger and structurally independent of the grains in the metal's crystal structure, metal particles (and devices made from such particles) can be made from alloys of any grain size. Thus, biodegradable implantable medical devices of the invention can be fabricated from powders made from any of the alloys described herein. The porosity resulting from the powdered-metal manufacturing technique, can be exploited, for example, by filling the pores of the medical devices with biodegradable polymers. The polymers can be used to retard the biodegradation rates of all or part of the implanted device, and/or mixed with bioactive agents (e.g., drugs) that enhance the healing of the tissue surrounding the device. If the porosity of the powdered metal device is filled with a drug, the drug will be delivered as it becomes exposed by the degradation of the device, thereby providing drug to the tissue site as long as the device remains present and biodegrading.

In certain embodiments, the implantable medical device is designed for implantation into a human. In other embodiments, the implantable medical device is designed for implantation into a pet (e.g., a dog, a cat). In other embodiments, the implantable medical device is designed for implantation into a farm animal (e.g., a cow, a horse, a sheep, a pig, etc.). In still other embodiments, the implantable medical device is designed for implantation into a zoo animal.

In another aspect, the invention provides a container containing an implantable medical device of the invention. In certain embodiments, the container is a packaging container, such as a box (e.g., a box for storing, selling, or shipping the device). In certain embodiments, the container further comprises an instruction (e.g., for using the implantable medical device for a medical procedure).

The following examples are intended to illustrate, but not to limit, the invention in any manner, shape, or form, either explicitly or implicitly. While the specific alloys described exemplify alloys that could be used in implantable medical devices of the invention, persons skilled in the art will be able to readily identify other suitable alloys in light of the present specification.

EXAMPLES

Example 1

A "condition A" martensitic steel composed of 0.23% carbon, 3.1% chromium, 11.1% nickel, 1.2% molybdenum, 13.4% cobalt and 70.97% iron was obtained from Carpenter Steel. The steel was heat treated it in a reducing atmosphere at 1250° C. for 12 hours, followed by slow cooling. Afterwards, the material was tested for Rockwell Hardness, yielding a hardness range of 31-32 on the Rockwell C scale. The steel was then cut into pieces of various dimensions:
(1) 0.514" width by 0.0315" length by 0.020" thick, having a surface to volume ratio of about 167.4 and weighing about 48.2 mg;

(2) 0.514" width by 0.0315" length by 0.050" thick, having a surface area to volume of about 107.4 and weighing about 119.8 mg; and (3) 0.514" width by 0.0315" width by 0.500" thick, having a surface to volume ratio of about 71.4 and weighing about 1207.7 mg.

Each piece of steel was immersed in 10 ml of human blood at 37° C. under gentle rocking. At one week intervals the pieces were retrieved, weighed and tested for Rockwell hardness. The test pieces demonstrated a degradation rate matching the linear formula L=0.74·S, where L is the loss in milligrams per day and S is the total surface area. No loss in hardness of the material was apparent up the point that the material thickness became too thin to measure, demonstrating that material loss was from the exterior surfaces with no degradation of the interior material.

Example 2

An austenite steel comprising 0.1% carbon, 0.45% manganese, and 99.45% iron and having no contaminating elements greater than 0.05% was obtained from a commercial source. The alloy was etched and tested for grain size and Rockwell hardness. The alloy was then cut into several pieces having dimensions of about 0.5" wide by about 0.5" long by about 0.005" thick.

The pieces of austenite steel were tested for hardness and then immersed in 10 CC of blood at 37° C. with gentile agitation. The pieces were removed at weekly intervals, weighed, tested for hardness and re-immersed in fresh blood for the next period. The resulting dissolution into the blood samples followed the linear formula L=1.05·S, where L is the loss in milligrams per day and S is the total surface area. No loss of hardness was apparent up to the point that material thickness became too thin to make a hardness measurement.

In both of the above experiments, the dissolution rate was largely a function of the total surface area which, due to the shape of the test pieces, changed very little throughout the experiment. In device shapes more consistent with practical implants, the surface of the device will be reduced in surface area as the device is dissolved and replaced with body tissues. The reduction in surface area will reduce the rate of metal loss, causing the ultimate loss curve to be a geometric function of the remaining device surface area. Thus, as persons skilled in the art will readily appreciate, rate of loss of an implanted device will largely be a function of the geometry of the device.

Example 3

Some examples of austenite alloys suitable for use in implantable medical devices of the invention are as follows:

| Alloy 1: | |
| --- | --- |
| Carbon | 0.1% |
| Nickel | 6.0% |
| Cobalt | 20.0% |
| Manganese | 1.0% |
| Chromium | 2.0% |
| Molydbenum | 2.0% |
| Iron | 68.9% |
| Alloy 2: | |
| Carbon | 0.1% |
| Nickel | 6.0% |
| Cobalt | 20.0% |
| Manganese | 8.0% |
| Chromium | 2.0% |
| Tantalum | 4.0% |
| Iron | 59.9% |
| Alloy 3: | |
| Carbon | 0.1% |
| Nickel | 0.0% |
| Cobalt | 20.0% |
| Manganese | 10.0% |
| Molydbenum | 2.0% |
| Tantalum | 4.0% |
| Iron | 63.9% |
| Alloy 4: | |
| Carbon | 0.08% |
| Nickel | 0.0% |
| Manganese | 28.0% |
| Titanium | 3.0% |
| Iron | 68.92% |

As persons skilled in the art will readily appreciate, the foregoing alloys may contain some impurities that cause the actual percentages of each element in the alloy to be slightly lower than shown above.

Example 4

Thin flat samples approximately 0.5 inches square and 0.05 inches thick were prepared from a martensitic steel composed of 0.23% carbon, 3.1% chromium, 11.1% nickel, 1.2% molybdenum, 13.4% cobalt, and the balance iron. The flat shape was chosen so that there would be very little change in surface area as the samples degraded. The samples were cleaned and weighed. All samples were then immersed in buffered saline at 37° C. with slow orbital shaking. Half of the samples were allowed to oxidize in air, forming protective chromium oxides on the surface prior to immersion, and the other half were immersed immediately after cleaning. Samples were removed at intervals between one week and 136 days dried and weighed. Samples that were immersed immediately after cleaning experienced a constant weight loss of 1.1 mg per square inch per day over the study period. Samples that were oxidized prior to immersion experienced a weight loss of 0.6 mg per day per square inch of surface. The protective effect of chromium oxide reduced the degradation rate by approximately 50%.

Example 5

An austenitic alloy composed of 0.08% carbon, 18% manganese, 5% cobalt, 0.5% molybdenum, 1% tantalum, and 2% chromium was melted, upset forged and hot rolled to approximately 0.094 inches thick. The alloy had a hardness of approximately Rockwell C 45. Samples were immersed in buffered saline at 37° C. with slow orbital shaking The samples were periodically rinsed, dried and weighed for a three month period. The samples experienced a constant weight loss of 1.07 mg per square inch per day.

Example 6

An austenitic alloy composed of 0.08% carbon, 18% manganese, 5% cobalt, 0.5% molybdenum, 1% tantalum, and 2% chromium was melted, upset forged and hot rolled to approximately 0.094 inches thick. The alloy was further annealed at 1800° F., after which the alloy had a hardness of approximately Rockwell C 25. Samples were immersed in buffered saline at 37° C. with slow orbital shaking The samples were periodically rinsed, dried and weighed for a three month period. The samples experienced a constant weight loss of 0.92 mg per square inch per day.

Example 7

An austenitic alloy composed of 0.08% carbon, 18% manganese, 5% cobalt, 0.5% molybdenum, 1% niobium, and 2% chromium was melted, upset forged and hot rolled to approximately 0.094 inches thick. The alloy had a hardness of approximately Rockwell C 45. Samples were immersed in buffered saline at 37° C. with slow orbital shaking The samples were periodically rinsed, dried and weighed for a three month period. The samples experienced a constant weight loss of 1.08 mg per square inch per day.

Example 8

An austenitic alloy composed of 0.08% carbon, 18% manganese, 5% cobalt, 0.5% molybdenum, 1% niobium, and 2% chromium was melted, upset forged and hot rolled to approximately 0.094 inches thick. The alloy was further annealed at 1800° F., after which the alloy had a hardness of approximately Rockwell C 25. Samples were immersed in buffered saline at 37° C. with slow orbital shaking The samples were periodically rinsed, dried and weighed for a three month period. The samples experienced a constant weight loss of 0.98 mg per square inch per day.

Although the invention has been described with reference to the presently preferred embodiments, it should be understood that various changes and modifications, as would be obvious to one skilled in the art, can be made without departing from the spirit of the invention. Accordingly, the invention is limited only by the following claims.

What is claimed:

1. An implantable medical device comprising a biodegradable alloy, wherein the alloy is substantially austenite in structure, wherein the alloy has an average grain size in the range of about 0.5 microns to about 20 microns and a reactive surface to volume ratio for individual grains of, on average, greater than $0.1\mu^{-1}$, wherein the average grain size is stable at minimum recrystallization temperature of 0.55 times the absolute melting temperature of the alloy and wherein the rate of dissolution from the exterior surface of the biodegradable alloy is substantially uniform at each point of the exterior surface.

2. The implantable medical device of claim 1, wherein the average grain size is about 0.5 microns to about 5.0 microns.

3. The implantable medical device of claim 1, wherein the average grain size is about 1.0 micron to about 2.0 microns.

4. The implantable medical device of claim 1, wherein the implantable device is a bone screw, bone anchor, tissue staple, craniomaxillofacial reconstruction plate, fastener, reconstructive dental implant, or stent.

5. The implantable medical device of claim 1, wherein the alloy comprises an austenite promoting component and a corrosion resisting component, and wherein the total amount of the austenite promoting component in the alloy is greater than about 10% and the total amount of the corrosion resisting component is about 0.5% to about 10%.

6. The implantable medical device of claim 1, wherein the alloy contains less than about 0.1% nickel and less than about 0.1% vanadium.

7. The implantable medical device of claim 1, wherein the alloy contains less than about 4% chromium.

8. The implantable medical device of claim 1, wherein the alloy contains less than about 6% cobalt.

9. The implantable medical device of claim 1, wherein the alloy contains less than about 0.1% nickel, less than about 0.1% vanadium, less than about 4% chromium, and less than about 6% of cobalt.

10. The implantable medical device of claim 1, wherein the alloy comprises an austenite promoting component comprising manganese, cobalt, platinum, palladium, iridium, aluminum, carbon, nitrogen, silicon, or any combination thereof, and wherein % platinum+% palladium+% iridium+0.5*(% manganese+% cobalt)+30*(% carbon+% nitrogen) is greater than about 12%.

11. The implantable medical device of claim 1, wherein the alloy comprises a corrosion resisting component comprising chromium, molybdenum, tungsten, tantalum, niobium, titanium, zirconium, hafnium, or any combination thereof, and wherein % chromium+% molybdenum+% tungsten+0.5*(% tantalum+% niobium)+2*(% titanium+% zirconium+% hafnium) is about 0.5% to about 7%.

12. The implantable medical device of claim 1, wherein the alloy comprises an austenite promoting component comprising manganese, cobalt, platinum, palladium, iridium, aluminum, carbon, nitrogen, silicon, or any combination thereof, wherein % platinum+% palladium+% iridium+0.5*(% manganese+% cobalt)+30*(% carbon+% nitrogen) is greater than about 12%, and wherein the alloy comprises a corrosion resisting component comprising chromium, molybdenum, tungsten, tantalum, niobium, titanium, zirconium, hafnium, or any combination thereof, wherein % chromium+% molybdenum+% tungsten+0.5*(% tantalum+% niobium)+2*(% titanium+% zirconium+% hafnium) is about 0.5% to about 7%.

13. The implantable medical device of claim 1, wherein the device is coated with a therapeutic agent.

14. The implantable medical device of claim 1, wherein the device is coated with a biodegradable hydrogel.

15. The implantable medical device of claim 1, wherein the device comprises a geometry that maximizes the surface to mass ratio.

16. The implantable medical device of claim 1, wherein the device comprises a hollow opening or passageway.

17. The implantable medical device of claim 1, wherein the biodegradable alloy comprises at least two non-iron metallic elements.

18. The implantable medical device of claim 1, wherein the biodegradable alloy comprises manganese and niobium.

19. The implantable medical device of claim 1, wherein the biodegradable alloy comprises at least about 0.01% to about 0.1% non-metallic element.

20. The implantable medical device of claim 1, wherein the biodegradable alloy comprises at least about 0.01% to about 0.1% carbon.

* * * * *